United States Patent [19]

Hagen et al.

[11] Patent Number: 5,198,575
[45] Date of Patent: Mar. 30, 1993

[54] PREPARATION OF NITROBENZOIC AND ANTHRANILIC ACIDS

[75] Inventors: Helmut Hagen, Frankenthal; Jacques Dupuis, Ludwigshafen, both of Fed. Rep. of Germany

[73] Assignee: BASF Aktiengesellschaft, Ludwigshafen, Fed. Rep. of Germany

[21] Appl. No.: 912,196

[22] Filed: Jul. 13, 1992

[30] Foreign Application Priority Data

Aug. 27, 1991 [DE] Fed. Rep. of Germany ....... 4128351

[51] Int. Cl.$^5$ .............................................. C07C 51/16
[52] U.S. Cl. .................................... 562/410; 562/456
[58] Field of Search ............................... 562/410, 456

[56] References Cited

U.S. PATENT DOCUMENTS 3,542,858 11/1970 Mulvey ................................. 562/410
3,723,523 3/1973 Horrom ................................ 562/410
4,454,345 6/1984 Jacques ................................ 562/410
4,994,606 2/1991 Fertel .................................. 562/456

FOREIGN PATENT DOCUMENTS 3409244 9/1985 Fed. Rep. of Germany .

Primary Examiner—Michael L. Shippen
Attorney, Agent, or Firm—Oblon, Spivak, McClelland, Maier & Neustadt

[57] ABSTRACT

Nitrobenzoic acids I

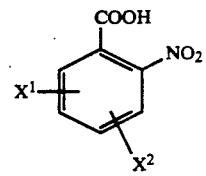

($X^1$, $X^2$=fluorine, chlorine, bromine, hydrogen or nitro) are prepared by oxidizing the corresponding nitrotoluene II

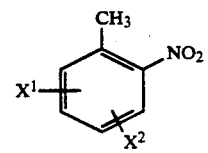

with nitric acid in the presence of sulfuric acid and vanadium(V) compounds, and anthranilic acids III

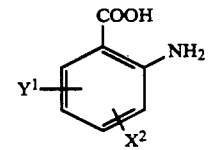

($Y^1$, $Y^2$=fluorine, chlorine, bromine, hydrogen or amino) are prepared from the nitrobenzoic acids I by reduction.

2 Claims, No Drawings

PREPARATION OF NITROBENZOIC AND ANTHRANILIC ACIDS

The present invention relates to an improved process for preparing nitrobenzoic acids of the general formula I

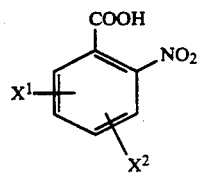

where $X^1$ and $X^2$ are each fluorine, chlorine, bromine, hydrogen or nitro, by oxidizing the corresponding nitrotoluene of the general formula II

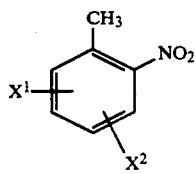

with nitric acid, and to the preparation of anthranilic acids of the general formula III

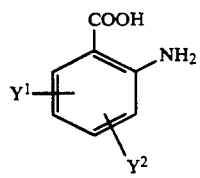

where $Y^1$ and $Y^2$ are each fluorine, chlorine, bromine, hydrogen or amino, by reducing the nitrobenzoic acids I obtained according to the invention.

Nitrobenzoic acids of the formula I are useful intermediates for preparing anthranilic acids of the formula III, which in turn are important starting compounds for dye synthesis. The nitrobenzoic acids I are, as will be known, obtainable by oxidizing the corresponding nitrotoluene II. In the process described in DE-A-34 09 244, this oxidation is carried out with dilute nitric acid at elevated temperature and pressure, necessitating the use of costly pressure-resistant reaction apparatus.

According to DE-A-34 09 244 the nitrobenzoic acids I can then be converted into the corresponding anthranilic acids III by catalytic hydrogenation.

It is an object of the present invention to make nitrobenzoic acids I available in good yields and good purities in a technically simple and economical manner and hence also to make possible an advantageous preparation of the anthranilic acids III.

We have found that this object is achieved by a process for preparing nitrobenzoic acids of the general formula I

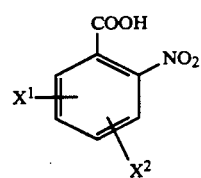

where $X^1$ and $X^2$ are each fluorine, chlorine, bromine, hydrogen or nitro, by oxidizing the corresponding nitrotoluene of the general formula II

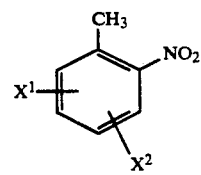

with nitric acid, which comprises carrying out the oxidation in the presence of sulfuric acid and vanadium(V) compounds.

The nitrobenzoic acids I prepared according to the invention are then, after their isolation, convertible into anthranilic acids of the formula III

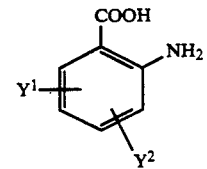

where $Y^1$ and $Y^2$ are each fluorine, chlorine, bromine, hydrogen or amino, by reduction.

Vanadium(V) compounds suitable for the process of the invention are preferably those which are soluble in acids, in particular in sulfuric acid or in mixtures of sulfuric acid and nitric acid, ie. as well as the nitrate and acetate preferably the sulfate and particularly preferably the oxide. They can be used individually or in the form of mixtures.

In general, from 0.01 to 0.2, preferably from 0.08 to 0.12, mole equivalents of vanadium(V) compound is used per mole of II.

The oxidation is preferably carried out in the presence of from 60 to 85% strength by weight sulfuric acid as reaction medium. The amount of sulfuric acid is freely choosable, but it is advisable to use from 0.5 to 3 mol, preferably from 1 to 2 mol, of sulfuric acid per mole of II.

The concentration of the nitric acid used for the oxidation according to the invention can vary within wide limits, but its concentration is advantageously from 40 to 100% by weight, preferably from 50 to 70% by weight. The amount of nitric acid is in general from 2 to 8, preferably from 3 to 5, mol per mole of II.

In general, the reaction is carried out at from 130 to 190° C, preferably at from 165 to 180° C.

It is of particular advantage that the reaction can be carried out under atmospheric pressure. However, the employment of superatmospheric pressure is not excluded.

The process is conveniently carried out by suspending the nitrotoluene II and the vanadium(V) compound in the sulfuric acid and adding the nitric acid after the suspension has been heated to about 130-190° C.

During the reaction, which in general takes from 8 to 12 hours, dilute nitric acid can be distilled off mixed with organic phase. The organic phase is then advantageously recycled into the reaction vessel.

The process of the invention can be carried out not only batchwise but also continuously, for example in a stirred kettle cascade.

The reaction mixture is preferably worked up for the nitrobenzoic acid I by repeated extraction with an acid-stable organic solvent, such as nitrobenzene, mono-, di- and trichlorobenzenes, in particular o-dichlorobenzene, at from 90 to 150° C, preferably at from 135 to 145° C. The nitrobenzoic acids I can be precipitated by cooling the resulting extract to about 0-5° C and isolated by conventional filtration.

Further purification of the product I is in general not necessary. On the contrary, they can be used directly with or without drying for further reactions. The purity is in general monitored by chromatography.

This type of workup has the advantage that not only the removed sulfuric acid phase but also the extractant can be repeatedly reused for reaction and for extraction respectively.

The process of the invention gives the nitrobenzoic acids I in a technically simple and hence economical manner in good yield and high purity.

The nitrobenzoic acids I prepared according to the invention are advantageous starting materials for preparing anthranilic acids III.

The necessary reduction can be effected in a manner known per se, preferably by catalytic hydrogenation (cf. Houben-Weyl, Methoden der Organischen Chemie, volume XI/1, pages 360–492 (1957)).

Suitable catalysts for this hydrogenation are in particular Raney nickel and palladium and also in particular platinum. Palladium and platinum are advantageously used in the form of a supported catalyst, preferably on carbon.

The catalytic hydrogenation is in general carried out in an alcohol, such as ethanol, propanol, isopropanol or in particular methanol, at from 20 to 60° C. under a hydrogen pressure of up to 2 bar.

After the hydrogenation has ended, the catalyst is advantageously removed by filtration. The anthranilic acids III can then be isolated by concentrating the filtrate or particularly advantageously by direct spray drying of the as-reduced solution.

The anthranilic acids III too are obtained in a sufficiently pure form for them to be directly usable for further purposes such as dye synthesis.

Preparing the anthranilic acids III by way of the novel oxidation of nitrotoluenes II and the subsequent reduction of the resulting nitrobenzoic acids I represents an advantageous synthesis route.

EXAMPLES

EXAMPLE 1

Preparation of 2-chloro-6-nitrobenzoic acid

A mixture of 343 g (2 mol) of 2-chloro-6-nitrotoluene, 80 g (0.4 mol) of vanadium pentoxide, 2609 g of 96% strength by weight sulfuric acid and 731 g of water was heated to 175° C. At that temperature 610 g (439 ml; 6.3 mol) of 65% strength by weight nitric acid were metered in over 10.5 h.

During this period a distillate receiver preheated to about 100° C. collected 347 g of distillate, of which the organic phase (a total of 37 g) was pumped back into the reaction vessel. On completion of the nitric acid addition the reaction mixture was stirred for 30 min and then cooled down to 140° C.

To isolate the target product the mixture was extracted once with 1000 ml and twice with 500 ml of o-dichlorobenzene. The combined organic phases (3005 g) were cooled down to 0-5° C. in a precipitation vessel in the course of about 4 h. The 2-chloro-6-nitrobenzoic acid thus precipitated was filtered off and dried at 50° C. under reduced pressure.

This gave 267 g of 2-chloro-6-nitrobenzoic acid with a purity of >98% (yield 65%), which was directly usable for synthesizing 6-chloroanthranilic acid.

EXAMPLE 2

Preparation of 6-chloroanthranilic acid 262 g (1.3 mol) of the 2-chloro-6-nitrobenzoic acid obtained in Example 1 were dissolved in 1583 g of methanol in a pressure-resistant vessel under nitrogen. Following addition of 25 g of a platinum catalyst (5% by weight of platinum on activated carbon) the vessel was sealed and purged with 1 l of hydrogen after the contents had been heated to 50° C. 7.8 g (87 l; 3.9 mol) of hydrogen were forced in under an overpressure of about 0.5 bar.

To isolate the target product, the catalyst was filtered off after hydrogen uptake had ceased, and the filtrate was spray dried.

This gave 225 g of 6-chloroanthranilic acid with a purity of >98%, which corresponds to a yield of 98%.

We claim:

1. A process for preparing nitrobenzoic acids of the general formula I

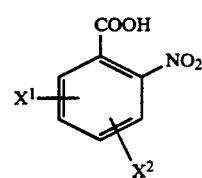

where $X^1$ and $X^2$ are each fluorine, chlorine, bromine, hydrogen or nitro, by oxidizing the corresponding nitrotoluene of the general formula II

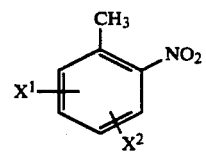

with nitric acid, which comprises carrying out the oxidation in the presence of sulfuric acid and vanadium(V) compounds.

2. A process for preparing anthranilic acids of the general formula III

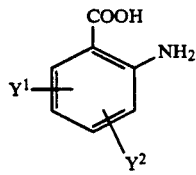

where $Y^1$ and $Y^2$ are each fluorine, chlorine, bromine, hydrogen or amino, by oxidizing the corresponding nitrotoluene of the general formula II

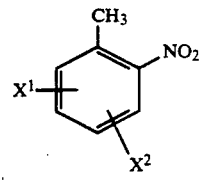

where $X^1$ and $X^2$ are each fluorine, chlorine, bromine, hydrogen or nitro, with nitric acid to obtain nitrobenzoic acid of the general formula I

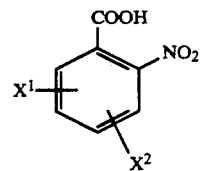

and isolating and subsequently reducing this nitrobenzoic acid, which comprises carrying out the oxidation in the presence of sulfuric acid and vanadium(V) compounds.

* * * * *